United States Patent
Head et al.

(10) Patent No.: US 9,211,322 B2
(45) Date of Patent: Dec. 15, 2015

(54) IMMUNOTHERAPEUTICAL METHOD FOR TREATING CANCER

(71) Applicant: OncBioMune, L.L.C., Baton Rouge, LA (US)

(72) Inventors: Jonathan F. Head, Baton Rouge, LA (US); Robert L. Elliott, Baton Rouge, LA (US)

(73) Assignee: ONCBIOMUNE, INC., Baton Rouge, LA (US)

( * ) Notice: Subject to any disclaimer, the term of this patent is extended or adjusted under 35 U.S.C. 154(b) by 0 days.

(21) Appl. No.: 14/137,060

(22) Filed: Dec. 20, 2013

(65) Prior Publication Data

US 2014/0112884 A1    Apr. 24, 2014

Related U.S. Application Data

(63) Continuation of application No. 13/005,993, filed on Jan. 13, 2011, now Pat. No. 8,647,627.

(51) Int. Cl.

| | | |
|---|---|---|
| *A61K 39/00* | (2006.01) | |
| *A61K 38/00* | (2006.01) | |
| *A61K 38/19* | (2006.01) | |
| *A61K 38/17* | (2006.01) | |
| *A61K 38/18* | (2006.01) | |
| *A61K 38/20* | (2006.01) | |
| *A61K 39/39* | (2006.01) | |

(52) U.S. Cl.
CPC .............. *A61K 39/0011* (2013.01); *A61K 38/17* (2013.01); *A61K 38/18* (2013.01); *A61K 38/20* (2013.01); *A61K 39/39* (2013.01)

(58) Field of Classification Search
None
See application file for complete search history.

(56) References Cited

U.S. PATENT DOCUMENTS

| | | | |
|---|---|---|---|
| 5,478,556 | A | 12/1995 | Elliott et al. |
| 6,312,718 | B1 | 11/2001 | Popescu et al. |
| 7,517,952 | B1 | 4/2009 | Xu et al. |
| 7,622,478 | B2 | 11/2009 | Tiwari et al. |
| 7,919,079 | B2 | 4/2011 | Simmons et al. |
| 2006/0035375 | A1 | 2/2006 | Head et al. |
| 2007/0128159 | A1 | 6/2007 | Vicari |
| 2011/0212090 | A1 | 9/2011 | Pedersen et al. |

FOREIGN PATENT DOCUMENTS

WO    2006/023598 A2    3/2006

OTHER PUBLICATIONS

Schlom, J. Recent Advances in Therapeutic Cancer Vaccines, Cancer Biotherapy and Radiopharmaceuticas 2012, 27 (1),2-5.
Cancer Vaccines—National Cancer Institute, http://www.cancer.gov/cancertopics/factsheelfTherapy/cancer-vaccines, last viewed Sep. 24, 2013, 12 pages.
International Preliminary Examination Report for PCT/US2012/020596, dated Jul. 25, 2013,5 pages.
PCT, Notification of Transmittal of the International Search Report and the Written Opinion of the International Searching Authority, in International application No. PCT/US2012/020596, dated May 24, 2012.
Database Biosis [Online] Biosciences Information Service, Philadelphia, PA, US; May 1, 2000, Meidenbauer N. et al.: "Generation of PSA-reactive effector cells after vaccination with a PSA-based vaccine in patients with prostate cancer", XP002674429, Database accession No. PREV200000220195 abstract. (2 pages).
Head et al., Evaluation of Lymphocyte Immunity in Breast Cancer Patients. Breast Cancer Res. Treat. 1993, 26, 77-88.
Head et al, Assessment of Immunological Competence and Host Reactivity Against Tumor Antigens in Breast Cancer Patients: Prognostic Value and Rationale of Immunotherapy Development. Ann. New York Acad. Sci. 1993, 690, 340-342.
Jiang et al., Immune Responses in Breast Cancer Patients Vaccinated with Autologous Tumor Cells, Allogeneic Tumor Cells and the Tumor Antigen CA 15-3. Cancer Biother Radiopharm. 2000,15,110.
Elliott et al., Comparison of estrogen and progesterone receptor status to lymphocyte immunity against tumor antigens in breast cancer patients. Breast Cancer Research and Treatment 1994, 30, 299-304.
Hsueh et al., Prolonged Survival After Complete Resection of Disseminated Melanoma and Active Immunotherapy with a Therapeutic Cancer Vaccine. J. Clin. Oncol. 2002, 20(23): 4549-54.
Galon et al., Type, Density, and Location of Immune Cells Within Human Colorectal Tumors Predict Clinical Outcome. Science 2006,313,1960-64.
Gehan et al., The Determination of the Number of Patients Required in a Preliminary and Follow-up Trial of a New Chemotherapeutic Agent. J. Chron. Dis. 1961, 13(4), 346-353.
Tarassoff et al., Therapeutic vaccines for prostate cancer, The Oncologist, 11,451-462,2006.
Meidenbauer et al. Generation of PSA-reactive effector cells after vaccination with a PSA-based vaccine in patients with prostate cancer—The Prostate, 43, 88-100, 2000.
Pavlenko et al., A phase I trial of DNA vaccination with a plasmid expressing prostate-specific antigen in patients with hormonerefractory prostate cancer, Brit. J. Cancer, 91, 688-694, 2004.

*Primary Examiner* — Elly-Gerald Stoica
(74) *Attorney, Agent, or Firm* — McAndrews Held & Malloy, Ltd.

(57) ABSTRACT

Pharmaceutical compositions useful as vaccines are described containing a purified surface or excreted protein qualitatively or quantitatively associated with a type of cancer, at least one interleukin (IL), and at least one colony stimulating factor (CSF), where the purified surface or excreted protein is provided in an amount sufficient to induce an immune response in an individual administered the composition. Such compositions can be used in methods for treating individuals having cancer, and for inducing an immunotherapeutic response in the same.

2 Claims, 1 Drawing Sheet

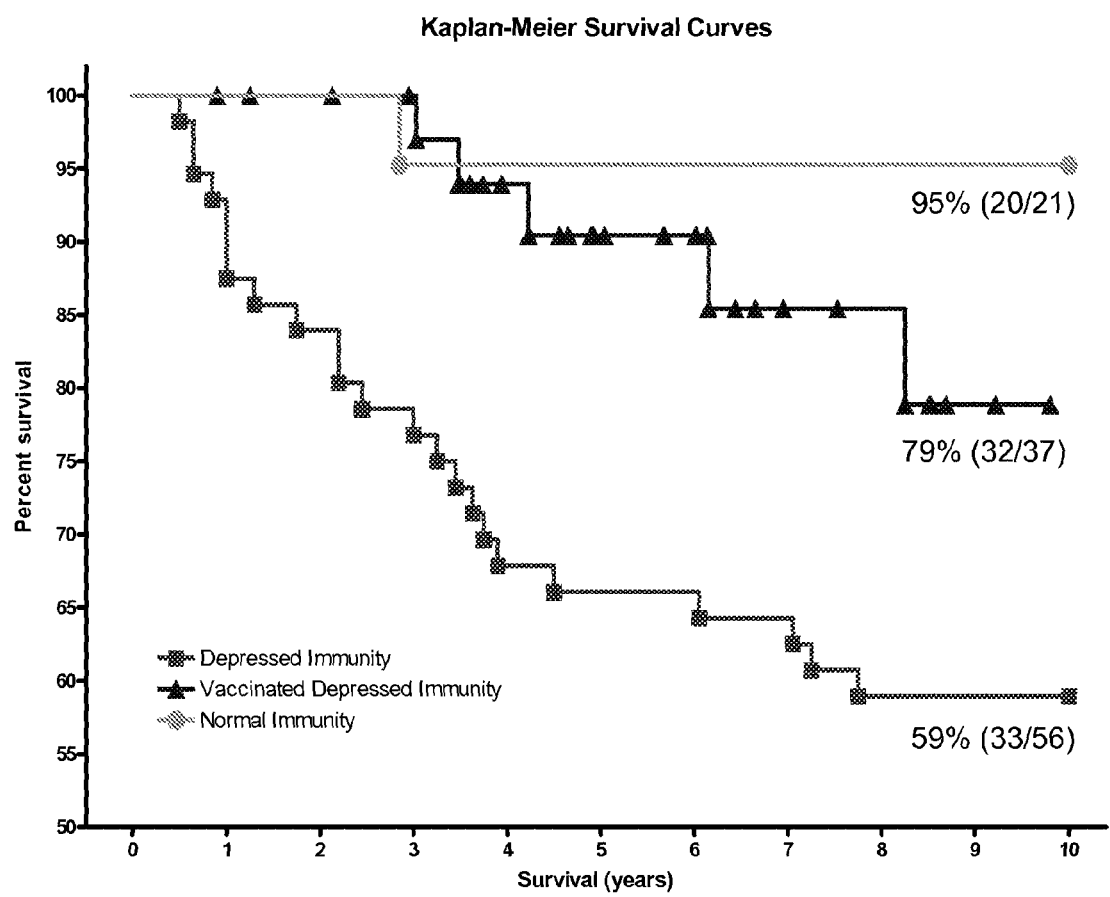

IMMUNOTHERAPEUTICAL METHOD FOR TREATING CANCER

CROSS-REFERENCE TO RELATED APPLICATIONS

This application is a continuation of U.S. patent application Ser. No. 13/005,993 having a filing date of Jan. 13, 2011, which is incorporated herein by reference in its entirety.

FIELD OF THE INVENTION

The present invention is directed to methods and compositions comprising purified surface or excreted proteins for treating cancer.

BACKGROUND OF THE INVENTION

The National Cancer Institute estimates that over 10 million Americans have a history of cancer. The American Cancer Society has predicted that over 1.4 million new cancer diagnoses will be made and over half a million Americans will die of cancer this year. Cancer is the second most common cause of death in the United States, exceeded only by heart disease.

Given the prevalence of various forms of cancer in this country, significant research focuses on developing new methods of diagnosis and treatment. Depending upon the type of cancer and its stage, current forms of treatment typically can include surgery, radiation, chemotherapy and/or hormonal treatments.

In recent years, research efforts also have focused on the development of cancer vaccines. Such vaccines are intended either to treat existing cancers (i.e., therapeutic vaccines) or to prevent cancer from developing (i.e., prophylactic vaccines). Therapeutic vaccines are designed to treat cancers by stimulating the immune system to recognize and attack cancer cells without damaging non-cancerous cells. Prophylactic vaccines are administered to healthy persons to stimulate their immune systems to attack cancer causing agents such as cancer causing viruses.

Currently, two vaccines have been licensed by the U.S. Food and Drug Administration to prevent viral infections that can lead to cancer. One is a vaccine which prevents infection with the hepatitis B virus, a virus associated with some forms of liver cancer; the second is a vaccine which prevents infection with two types of human papilloma virus that together cause 70 percent of cervical cancer cases.

Progress in developing therapeutic cancer vaccines has come more slowly. Efforts have been made to vaccinate cancer patients with tumor cells or tumor-associated antigens. Some of these efforts have had limited success. An example of a class of vaccines is reported in U.S. Pat. No. 5,478,556, which describes vaccinating breast cancer patients with compositions comprising a combination of extracted autologous or allogeneic breast tumor associated antigens (TAA) obtained from cancer cells, interleukin-2 (IL-2), and granulocyte macrophage colony stimulating factor (GM-CSF).

SUMMARY OF THE INVENTION

In one aspect, compositions are provided comprising (i) a purified surface or excreted protein qualitatively or quantitatively associated with a type of cancer; (ii) at least one interleukin (IL); and (iii) at least one colony stimulating factor (CSF), wherein the protein is provided in an amount sufficient to induce an immune response in an individual administered the composition.

In another aspect, methods for treating an individual are provided comprising administering to an individual having a type of cancer, a therapeutically effective amount of a composition of the preceding aspect.

In another aspect, methods for inducing an immunotherapeutic response in an individual are provided comprising administering to an individual diagnosed with a type of cancer a therapeutically effective amount of a composition of the preceding aspect (supra), wherein the composition comprises the purified surface or excreted protein in an amount sufficient to induce an immunotherapeutic response in the individual.

BRIEF DESCRIPTION OF THE DRAWINGS

FIG. 1 is a Kaplan-Meier Overall Survival Curve with patients who died of other causes censured for Reference Example 1.

DETAILED DESCRIPTION OF THE INVENTION

The present disclosure provides methods and compositions useful for the treatment of cancer. Thereby, in accordance with the present disclosure, a patient suffering from a type of cancer is administered a therapeutically effective amount of a composition comprising a purified surface or excreted protein which is qualitatively or quantitatively associated with that cancer type in combination with adjuvants comprising an interleukin (IL) and a colony stimulating factor (CSF).

The disclosure further is directed to cancer vaccine compositions comprising a purified surface or excreted protein qualitatively or quantitatively associated with particular types of cancer in combination with biological adjuvants comprising an interleukin and a colony stimulating factor.

Without being limited by any one mechanism of action, it is believed that the composition acts by causing tumor cell death, inhibiting tumor growth or recurrence, promoting tumor regression and/or inhibition of metastasis, leading to an increase in disease-free survival rate and/or overall survival rate; or any combination thereof.

In certain embodiments, the interleukin is interleukin-2 (IL-2) and the colony stimulating factor is granulocyte-macrophage CSF (GM-CSF).

The immune response of a patient receiving the vaccine can be measured prior to the first vaccination and then measured again after the first vaccination and, if desired, after any subsequent vaccination to determine the extent of the immune response. The level of immune response can be quantified with the Lymphocyte Blastogenesis Assay (LBA) (see Elliott, R. et al., *Breast Cancer Research and Treatment* 30:299-304 (1994); herein incorporated by reference). In this assay, mononuclear cells are grown in tissue culture for seven days. The mononuclear cells are co-cultured with tumor antigen in varying concentrations. $^3$H-thymidine is added to the cultures shortly before termination. A proliferation index is then calculated by dividing the amount of $^3$H-thymidine uptake incorporated into tumor antigen-stimulated mononuclear cells in culture by the $^3$H-thymidine uptake incorporated into control mononuclear cells, which were not co-cultured with tumor antigen.

As used herein, the phrase "therapeutically effective amount" refers to the amount of the referenced compound or composition that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

For example, a therapeutically effective amount of a compound or composition can be measured as an amount that increases the immune response to tumor antigens by at least 50%; or stabilizes or decreases circulating tumor marker proteins resulting in inhibiting the progression of the cancer.

As used here, the terms "treatment" and "treating" means (i) ameliorating, inhibiting, or preventing the referenced disease state, as described above; or (ii) eliciting the referenced biological effect (e.g., an immunotherapeutic reaction can result in an alleviation or arrest of the disease from which the patient of interest is suffering). More specifically, treating can include inhibiting tumor growth or recurrence, regressing a tumor and/or inhibiting formation of metastases.

As used herein, reference to "a" or "an" or "the" protein or antigen or adjuvant can refer to one or more than one protein or antigen or adjuvant. As used herein, a surface or excreted protein which is "qualitatively or quantitatively associated with" a cancer type means a protein which is either typically found only on the surface of, or excreted by, one or more particular types of cancer or is found on the surface of, or excreted by, cancer cells more abundantly than normal or non-cancerous cells. Such proteins also are known as tumor marker proteins or tumor associated antigens, and these terms are used interchangeably within the application. These proteins can be purified from a tumor cell preparation or can be synthesized by methods known to persons of skill in the art. Further, these proteins can be prepared as a mixture with other non-tumor associated proteins, or can be prepared in a preparation where they are the only protein component.

Examples of such proteins or antigens, and the cancers with which they are associated, include those listed in Table 1 below:

TABLE 1

| Cancer | Proteins & Antigens |
| --- | --- |
| prostate | PSA, prostatic acid phosphatase (PAP), prostate specific membrane antigen (PSMA), carcino-embryonic antigen (CEA), cancer antigen (CA) 125 |
| breast | CA 15-3, CA 27.29, CEA, CA 125, estrogen receptor (ER), progesterone receptor (PgR), human epidermal growth factor receptor 2 (Her-2/neu), lipid-associated sialic acid in plasma (LASA-P) |
| gastrointestinal | CEA, CA 19-9, α-feto protein (AFP), CA 72-4, bladder tumor antigen (BTA), tissue polypeptide antigen (TPA) |
| lung | CEA, AFP, neuron-specific enolase (NSE), chromogranin A, TPA, CA 72-4 |
| liver | CEA, CA 19-9, AFP, CA 50 |
| pancreatic | CEA, CA 19-9, AFP |
| thyroid | CEA, calcitonin, thyroglobulin |
| ovarian | CA 125, AFP, LASA-P, CA 50, CA 72-4 |

TABLE 1-continued

| Cancer | Proteins & Antigens |
| --- | --- |
| melanoma | S-100 proteins (S-100), tumor-associated antigen 90 (TA-90) |
| testicular | AFP, β Human chorionic gonadotropin (β-hCG); |
| leukemia | β-2 microglobulin, LASA-P |
| colorectal | CEA, CA 19-9, LASA-P |
| bladder | BTA, nuclear matrix protein 22 (NMP 22), TPA |
| lymphoma: | LASA-P |
| endometrial | ER, PgR |
| nervous system | calcitonin, chromogranin A, NSE |
| embryonic | β-hCG |

The compositions can be made from isolated and purified autologous, allogeneic or recombinant surface or excreted tumor marker proteins, or a combination thereof. These compositions have been found to be useful as cancer vaccines when administered in combination with low doses of an interleukin and a CSF.

In one embodiment, the composition comprises IL-2 and GM-CSF.

The use of isolated and purified antigens to the particular type of cancer to be treated provides more specificity and eliminates the variability present in the prior art vaccine compositions. Furthermore, preparation of the present vaccine does not require tissue from the patient and therefore every patient at presentation or after surgery is a candidate for the therapeutic vaccine. However, if desired, tissue from a patient can be used to make the present vaccine. The use of isolated and purified antigens also allows the vaccine compositions to be mass produced.

As used herein, the term "purified" means that the referenced entity has a purity of greater than about 50% by total weight. That is, in certain embodiments, each of the isolated and purified antigens used herein, independently, have a purity of greater than about 50% by total weight; or greater than about 60% by weight; or about 70% by weight; or about 80% by weight; or about 85% by weight; or about 90% by weight; or about 95% by weight; or about 98% by weight; or about 99% by weight.

The term "about" as used herein means+/−10% of the referenced value.

The compositions can be administered to patients suffering from solid tumors, malignant ascites or hemopoietic cancers to inhibit tumor growth or recurrence or to inhibit formation of metastases. The compositions also can be administered to patients suffering from leukemia or lymphoma.

Vaccine compositions are made using tumor marker proteins. Desired isolated and purified tumor marker proteins are available commercially. Sources of many of the antigens listed above include Fitzgerald Industries International, Concord, Mass., and Sigma-Aldrich Co, Dallas, Tex. Other commercial sources are known and available to persons of skill in the art. If any particular antigen is not commercially available, it can be synthesized in a cGMP facility according to methods known by persons of skill in the art.

Each of the tumor marker protein(s) are independently present in amounts typically ranging from about 1 µg to about 1000 µg per 100 µL of vaccine composition, or about 1 µg to about 250 µg per 100 µL of composition, or about 25 to about 100 µg per 100 µL of composition, or about 50 µg per 100 µL of composition, or about 1 µg to about 10 µg per 100 µL. If a particular antigen is not readily available or is not readily available at a reasonable cost, smaller amounts within the preceding ranges, such as within the range of about 1 µg to about 10 µg per 100 µL, can be used with good effect.

Some tumor marker proteins are sold on the basis of international units (IU), rather than μg. In such an instance, the antigen typically is provided in an amount within the range of 1 IU to about 10,000 IU per 100 μL of vaccine composition; or about 20 to about 5,000 IU, per 100 μL of composition; or about 500 IU to about 1500 IU per 100 μL of composition, or about 1000 IU per 1000 μL of composition.

For example, if the type of cancer of interest is prostate cancer and PSA is included in the vaccine composition, PSA can be provided at a concentration of about 1 μg to about 250 μg per 100 μL of composition, or about 25 μg to about 100 μg per 100 μL of composition, or about 50 μg per 100 μL of composition. PSA can be the sole marker in the prostate cancer vaccine, or the vaccine can comprise one or more additional or alternative antigens as indicated above.

The vaccine, for example, can also comprise CEA; this antigen typically is provided at a concentration of about 1 μg to about 250 μg per 100 μL of composition. CA 125 protein can be included in the vaccine; it typically is sold in the form of IU and can be provided at a concentration of from about 20 IU to about 5,000 IU per 100 μL of composition, or from about 100 IU to about 2500 IU per 100 μL of composition, or about 1000 IU, per 100 μL of composition.

CA 15-3 and/or CA 27.29 can be included, each at a concentration of about 1 μg to about 250 μg per 100 μL of composition.

Generally, the amount of a particular antigen used in the vaccine remains about the same whether the antigen is the sole antigen provided in the vaccine or is one of a number of antigens provided in the vaccine composition. Thus, in the prostate cancer vaccine example provided in the preceding paragraph, whether the composition comprises one of the antigens indicated or a combination of two, three, four or five antigens, each antigen is provided in an amount within the guidelines set forth above. The presence of additional antigens can increase the probability of an effective immune response in the patient.

In another embodiment, the purified antigen(s) are physically combined with small amounts of a combination of an interleukin and CSF. In another embodiment, the antigen solution and the adjuvants (e.g., the interleukin and CSF) are administered separately, but the antigens and adjuvants should be administered to the same site as close together in time as possible and no more than 2 hours apart. Typically, each component of the vaccine is provided in the form of a physiologically acceptable solution and then desired amounts of each solution are combined to make the final vaccine composition.

Suitable interleukins include IL-1, IL-2, IL-3, IL-4, IL-5, IL-6, IL-7, IL-9, IL-12, IL-13, IL-14 and IL-15. In certain embodiments, the interleukin is IL-1. In certain other embodiments, the interleukin is IL-2. In certain other embodiments, the interleukin is IL-3. In certain other embodiments, the interleukin is IL-4. In certain other embodiments, the interleukin is IL-5. In certain other embodiments, the interleukin is IL-6. In certain other embodiments, the interleukin is IL-7. In certain other embodiments, the interleukin is IL-9. In certain other embodiments, the interleukin is IL-12. In certain other embodiments, the interleukin is IL-13. In certain other embodiments, the interleukin is IL-14. In certain other embodiments, the interleukin is IL-15.

Suitable colony stimulating factors include granulocyte-macrophage-CSF (GM-CSF), granulocyte-CSF (G-CSF) and macrophage-CSF (M-CSF). In certain embodiments, the colony stimulating factor is GM-CSF. In certain embodiments, the colony stimulating factor is G-CSF. In certain embodiments, the colony stimulating factor is M-CSF.

A single interleukin and a single colony stimulating factor can be used in the compositions herein or a combination of two or more interleukins and/or colony stimulating factors can be used. Although the effectiveness of each type of cytokine is very limited if administered alone, the administration of both an interleukin and a CSF in combination with the tumor marker antigens has been found to have a synergistic effect.

In one embodiment, a combination of cytokines is GM-CSF and IL-2. The IL-2 promotes cytotoxic T-cell immunity; the GM-CSF promotes dendritic cell processing.

Typically, the composition comprises from about 5,000 U to about 50,000 Units (U) (about 0.3 μg to about 3 μg) of the interleukin per 100 μL of composition; or from about 10,000 U to about 30,000 U (about 0.6 μg to about 1.8 μg) of the interleukin per 100 μL of composition; or about 20,000 U (about 1.2 μg) of the interleukin per 100 μL of composition and about 10 μg to about 100 μg of the CSF per 100 μL of composition, or about 15 to about 20 μg of the CSF per 100 μL of composition, or about 16.5 μg to about 16.9 μg of the CSF per 100 μL of composition, or about 16.7 μg of the CSF per 100 μL of composition.

Typically, each cytokine is supplied as a lyophilized powder and combined with a physiologically acceptable liquid carrier and serially diluted if necessary to reach the final desired concentration in 100 μL. IL-2, for example, can be obtained under the name Proleukin® from Chiron Corporation, Emeryville, Calif., as a lyophilized powder, $22 \times 10^6$ IU (1.3 mg)/vial. If, for example, it is combined with 1.1 mL of sterile water and then serially diluted 1:10, 1:10 (final 1:100), its final concentration is 20,000 IU (1.18 μg) in 100 μL. Similarly, GM-CSF can be obtained under the name Leukine® from Berlex Laboratories, Montville, N.J., as a lyophilized powder, 250 μg/vial. If, for example, it is combined with 1.5 mL of sterile water, a final concentration of 16.7 μg per 100 μL will be obtained.

Suitable pharmaceutically acceptable carriers for the compositions herein refer to fluid vehicles that can be injected into a host without significant adverse effects. Suitable pharmaceutically acceptable carriers known in the art include, but are not limited to, sterile water, saline, glucose, and physiologically acceptable aqueous buffers or solutions, including saline or phosphate-buffered saline. Carriers may include auxiliary agents including, but not limited to, diluents, stabilizers (i.e., sugars and amino acids), preservatives, wetting agents, emulsifying agents, pH buffering agents, viscosity enhancing additives, colors and the like. For example, suitable carriers for the tumor marker proteins and the adjuvants include physiologically acceptable aqueous buffers or solutions, including sterile water, saline, phosphate-buffered saline, or Hank's buffered salt solution (HBSS).

Appropriate amounts of the antigens or adjuvants are mixed with the selected carrier. All of the components of the vaccine can be provided together in one carrier, but if desired, one or more components can be provided in a separate carrier and administered in combination with the other components.

In another aspect the disclosure provides methods for treating cancer which comprises administering a therapeutically effective amount of a composition comprising a purified surface or excreted protein which is qualitatively or quantitatively associated with the cancer type in combination with biological adjuvants comprising an interleukin (IL) and a colony stimulating factor (CSF).

The vaccine can be administered by injection. In another embodiment, the vaccine is administered subcuticularly, but it also can be administered intramuscularly, subcutaneously, or intraperitoneal. The vaccine typically is administered in doses of about 0.3 mL to about 1 mL, or about 0.5 mL to about 0.7 mL, or about 0.5 mL, per dose. Although a single dose of the vaccine may be useful, often times it is desirable to administer from about 3 to about 12 doses of the vaccine and or about 6 to about 12 doses. If more than one dose is administered, the doses typically are at least 7 days apart. For example, the doses typically can be administered about 7 to about 90 days apart. For example, one useful regimen is to administer three doses of the vaccine at weekly intervals, then to administer a further three doses at four week intervals after that (i.e., the vaccine is administered at weeks 0, 1, 2, 6, 10 and 14). If desired, booster shots can be administered monthly or bi-monthly for up to about one year following the initial immunization therapy. The booster shots can be alternated with booster shots of interleukin, such as, but not limited to, IL-2, to boost the patient's natural killer cells.

The T- and B-cell immunity of a patient receiving a vaccine in accordance with this disclosure can be monitored using a lymphocyte blastogenesis assay (see Elliott, R. et al., *Breast Cancer Research and Treatment* 30:299-304 (1994); herein incorporated by reference) before beginning the vaccine administration and then during and after the vaccine regimen. An increase in the proliferation index demonstrates an increase in the immune response to the cellular and protein antigens by the vaccination process. A patient receiving a vaccine in accordance with this disclosure can also be monitored with an assay measuring circulating tumor marker proteins. A decrease in circulating tumor marker proteins is a surrogate marker for an increase in the immune response.

The vaccines herein are useful for the treatment of any solid cancer, including cancers of the prostate, breast, lung, colon, rectum, uterus (including cervix and endometrium), ovary, oral cavity, bladder, pancreas, stomach, liver, kidney, skin, testicles and lymphoid tissue. They also can be used to treat malignant ascites and hematopoietic tumors, including leukemias and lymphomas. Appropriate tumor marker proteins are selected, and the vaccine is prepared using the general amounts of the components of the vaccine as set forth above.

In one embodiment, compositions are provided that are useful as a prostate cancer vaccine which comprise at least one purified surface or excreted protein qualitatively or quantitatively associated with prostate cancer combined with a combination of biological adjuvants, wherein the adjuvants consist essentially of an interleukin and a colony stimulating factor. In one embodiment, at least one purified surface or excreted protein comprises purified PSA, optionally in combination with one or more other purified proteins associated with prostate cancer. In a related embodiment, a method is provided for treating a person with prostate cancer which comprises immunizing the person with a composition comprising purified PSA, optionally in combination with one or more other purified proteins associated with prostate cancer, and biological adjuvants comprising an interleukin and a colony stimulating factor. In a further related embodiment, a method is provided for eliciting in a human with prostate cancer an immunotherapeutic response, wherein the immunotherapeutic response results in a decrease in circulating PSA and death to tumor cells, by immunizing the person with a composition comprising purified PSA, optionally in combination with other purified proteins associated with prostate cancer, and biological adjuvants, wherein the adjuvants consist essentially of an interleukin and a colony stimulating factor. The immunizations can be carried out once or, can be repeated. The immunization is designed to increase the immunotherapeutic response to the tumor antigens/proteins by a minimum of about 50% over baseline immunity, decrease circulating PSA, and result in tumor cell death, increased progression free survival and overall survival.

Another embodiment includes compositions useful as a breast cancer vaccine, comprising therapeutically effective amounts of purified surface or excreted proteins qualitatively or quantitatively associated with cancer of the breast. Such compositions can include CA 15-3, CA 125 or CEA, or a combination thereof, together with the above combination of biological adjuvants. In a related embodiment, a method is provided for treating a person with breast cancer which comprises immunizing the person with a composition comprising purified CA 15-3, CA 125 and CEA, optionally in combination with one or more other purified proteins associated with breast cancer, and biological adjuvants comprising an interleukin and a colony stimulating factor. The immunizations can be carried out once or can be repeated. The immunization is designed to increase the immunotherapeutic response to the tumor antigens/proteins by a minimum of about 50% over baseline immunity, decrease circulating tumor antigens, and result in tumor cell death, increased progression free survival and overall survival.

Other embodiments include compositions comprising therapeutically effective amounts of purified proteins qualitatively or quantitatively associated with cancer of the gastrointestinal system, lung, liver, pancreas, thyroid, ovaries, testicles, colorectal system, endometrium, bladder or nervous system, or melanoma, leukemia or lymphoma, and the administration of these compositions to persons suffering from such cancer to elicit an immune response to the cancer.

The disclosure is further illustrated by the following examples, which are not intended to be limiting.

EXAMPLES

Reference Example 1

A retrospective study was performed to determine the relationship between immune response and overall survival. Immune response was measured with the LBA, as discussed above.

The study was performed on early stage breast cancer patients with depressed immunity who had received a breast cancer vaccine in the adjuvant setting. The patients were tested for immune responses to autologous cells, allogeneic cells and protein antigens. Patients with depressed immunity, a ratio less than 1.5 (determined by cut point analysis of data set (Head, et al., Ann. NY Acad. Sci, 1993; 690: 340-342) of present modified LBA assay) in the LBA, were vaccinated with a minimum of six vaccines containing autologous breast cancer cells, allogeneic breast cancer cells (MCF-7 cells), CA 15-3 antigen, CA 125 antigen, CEA antigen and biological adjuvants (IL-2 and GM-CSF). A second LBA was done 2 to 4 weeks after the $6^{th}$ vaccination. The follow-up has been for up to 10 years. FIG. 1 is the Kaplan-Meier Overall Survival Curve with patients who died of other causes censured. The calculated Kaplan Meier overall survival (i.e., the percent survival over a continuous time period) for the patients at 10 years is 59% in depressed patients with standard treatment, and 95% survival for patients with immunity to their own tumor associated antigens in a LBA at presentation with standard treatment (historic controls for study). Depressed immunity patients lacking immunity to their own tumor antigens at presentation were vaccinated as stated above and this lead to an increase in overall survival from 59% to 79% at 10 years. The groups were well matched for age, menopausal status, tumor size, nodal status, stage of disease, estrogen receptor status, progesterone receptor status and antihormone therapy This study shows that patients with depressed immunity have a lower overall survival and a poor long-term prognosis when compared to patients with normal immunity, and further, that improving the immune response through vaccination improves overall survival.

Further, it is generally known in the art that an increase in immune response correlates to increase in overall survival. For instance, Hsueh et al. (J. Clin. Oncol., Dec. 1, 2002; 20(23): 4549-54), incorporated herein by reference, states "[s]urvival after vaccine immunotherapy was significantly correlated with the DTH immune response to vaccine but not to a control antigen . . . " (p. 4553, first paragraph of Discussion). In addition, Galon et al. (Science, Sep. 29, 2006; 313: 1960-64), incorporated herein by reference, reported that the " . . . time to recurrence and overall survival time are governed in large part by the state of the local adaptive immune response" (p. 1963, last paragraph).

Therefore, it is both known in the art and demonstrated by the data in FIG. 1, that an improved immune response correlates with overall survival in cancer patients.

Example 1

Preparation of PSA Composition

A composition in accordance with the present disclosure was made in accordance with the following procedure:

1. One mg of PSA (Fitzgerald Industries International, Concord, Mass., CAT #30-AP15E) was diluted in 2.0 mL of sterile water USP. The solution was filter sterilized with a 0.22 micron filter. 100 µL sterile aliquots were frozen at −80° C. until needed.

2. 500 µg of CEA (Fitzgerald Industries International, Concord, Mass., CAT #30-AC30) were diluted in 25 mL sterile water USP and the resultant solution was filter sterilized with a 0.22 micron filter. 100 µL sterile aliquots were frozen at −80° C. until needed.

3. 20,000 units of CA 125 (Fitzgerald Industries International, Concord, Mass., CAT #30-AC11) were diluted in 2.0 mL sterile water USP and the resultant solution was filter sterilized with a 0.22 micron filter. 100 µL sterile aliquots were frozen at −80° C. until needed.

4. 22 million units of IL-2 (Proleukin; Chiron Corporation, Emeryville, Calif.) were reconstituted in 1.1 mL sterile water USP, then diluted 1:10 with sterile water USP. The resultant solution was diluted 1:10 again to provide a final concentration of 20,000 units per 100 µL. Sterile aliquots of 100 µL were frozen at −80° C. until needed.

5. A vial of 250 µg GM-CSF (Berlex Laboratories, Montville, N.J.) was reconstituted with 1.5 mL sterile water USP to provide a final concentration of 16.7 µg in 100 µL. The solution was refrigerated at 4° C.

6. To prepare a dose of the vaccine, frozen aliquots of the following were brought to room temperature: 100 µL of each of the three antigens (PSA, CEA and CA 125) and 100 µL of each of the two adjuvants (IL-2 and GM-CSF). Then 100 µL of each component were drawn into a 1 mL syringe with a one inch 26 gauge needle. The final total volume was 0.5 mL. Each dose of vaccine contained 50 µg PSA; 2 µg CEA; 1000 IU CA 125; 20,000 units IL-2; and 16.7 µg GM-CSF.

Example 2

Thirteen biopsy-confirmed prostate cancer patients were administered subcuticularly at 0, 1, 2, 6, 10 and 14 weeks an initial course of 6 vaccinations, each dose containing PSA, CEA, CA 125, IL-2 and GM-CSF, prepared as in Example 1. Each patient's serum PSA level was determined before the first vaccine was initiated. During the vaccination period the patients received no other concurrent therapy (i.e., surgery, hormones, radiation, radioactive seeds or chemotherapy).

The treatment protocol was designed according to the scheme taught by Gehan (see Gehan, E., J. Chron. Dis. 13(4), 346-353 (1961); incorporated herein by reference) for determining the minimum response rates for oncology drugs in single arm Phase I/II clinical trials. Briefly, Gehan's method calculated the minimum sample size required without any responses to terminate the study because a predetermined minimum response rate (typically 15 to 20%) will not be reached. The confidence level was set at 95% and thus the study would be terminated early if there was 95% confidence that the response rate was less than the target response rate of 15 to 20%. Therefore, if 14 patients for 20% response rate or 19 patients for 15% response rate are treated without any responses then the drug is inactive. If one patient responds, then more patients need to be treated to determine an accurate response rate.

The results of the administration of the prostate cancer vaccine are provided in Table 2 below:

TABLE 2

| DIAGNOSIS | PSA BEFORE VACCINE | PSA AFTER 6 VACCINES | PSA AFTER 12 VACCINES | LAST PSA (months) |
|---|---|---|---|---|
| Prostate Cancer | 4.10 | 2.40 | 2.50 | 3.50 (80) |
| Prostate Cancer | 1.40 | 0.60 | 0.66 | 0.90 (92) |
| Prostate Cancer | 6.80 | 6.40 | only 6 vaccines | — |
| Prostate Cancer | 4.90 | 2.80 | 2.40 | 2.97 (42) |
| Prostate Cancer | 6.20 | 5.80 | 1.90 | 2.20 (65) |
| Prostate Cancer | 4.20 | 3.50 | 4.40 | 3.90 (18) |
| Prostate Cancer | 14.60 | 5.50 | 6.50 | 7.70 (49) |
| Prostate Cancer | 7.6 | 13.70 | only 4 vaccines | — |
| Prostate Cancer | 4.00 | 4.93 | seed implants | — |
| Prostate Cancer | 8.95 | 10.60 | 17.19 | Zoladex, seeds |
| Prostate Cancer | 7.20 | 5.41 | 7.30 | 6.00 (28) |
| Prostate Cancer | 4.55 | 7.02 | 4.17 | 10.80 (21) |
| Prostate Cancer | 5.40 | 10.40 | Lupron | — |

The PSA level of patient #8 rose from 7.6 to 13.7 after the fourth vaccination and he withdrew from the study to seek other therapy. The serum PSA level of each of the remaining 12 prostate cancer patients was determined 3-4 weeks after the 6$^{th}$ vaccination. As shown in Table 2, there was a decrease in serum PSA level in 8 of the 12 patients after the 6$^{th}$ vaccination.

One patient (patient #3), whose PSA had dropped from 6.8 to 6.4 and previously had received radiotherapy (the only patient previously treated), elected to withdraw from the study at the end of this initial vaccination period and underwent a radical prostatectomy. Two patients with rising PSAs after 6 vaccines elected to have additional standard therapy (one patient received seed implants and the other Lupron). Nine of the original 13 patients received 3 further doses of the vaccine alternated with doses of IL-2 (11 million units) to boost their natural killer cells for the 6 months following the initial vaccinations. One of these patients with a rising PSA elected to take Zoladex and seed implants. Eight patients have been followed for 18-92 months (variation in follow-up is due to the initial vaccination date of each patient (the patients entered into the trial at different times) and patients being lost to follow-up). The mean PSA value for these 8 patients was initially 5.9; it decreased to 4.1 after the initial 6 vaccines, decreased further to 3.7 after the 12 vaccines and was 4.7 after a mean follow-up time of 49 months (median of 45.5 months).

One patient, whose PSA decreased from 4.1 to a normal 2.4 ng/ml after vaccination, was re-biopsied after 18 and 30 months without cancer being found and has remained disease free and stable for over 10 years. Two other patients also have been re-biopsied subsequent to the vaccination process: one had no disease in the biopsy sample at 24 months and the other had a very significant decrease in the percentage of the biopsy sample containing cancer cells (from 55% to 1%) at 16 months.

The prostate cancer vaccine, described above, had immunological responses (as demonstrated by decreased serum PSA in 8 of 12 (67%) patients after six vaccines and 6 of 9 (67%) patients after 12 vaccines. Of the original 13 patients who enrolled in the trial 7 (54%) patients had PSA levels lower than at presentation after a median of 45.5 months (range of 18 to 80 months) of follow-up which is indicative of no biochemical progression of their disease (no increase in the amount of serum PSA). These response rates, as measured by decreases in the biological tumor marker PSA serum concentration, are estimated at 50% or better and therefore reflect a very significant response rate, according to the Gehan protocol. There is a slight increase in many of the prostate cancer patients PSA over time, and this suggests the need for booster vaccines after the initial 12 vaccines.

Example 3

The vaccines provided herein also are used to treat patients with other forms of cancer. Vaccine compositions are made using the following components following the general procedure in Example 1, as shown in Table 3.

TABLE 3

| Cancer | Marker 1 | Marker 2 | Marker 3 | IL | CSF |
|---|---|---|---|---|---|
| breast | 50 µg CEA | 50 µg CA 15-3 | 1000 IU CA 125 | 20,000 units IL-2 | 16.7 µg GM-CSF |
| gastrointestinal | 50 µg CEA | 50 µg CA 19-9 | 50 µg alpha Fetoprotein | 20,000 units IL-2 | 16.7 µg GM-CSF |
| liver | 50 µg CEA | 50 µg CA 19-9 | 50 µg alpha Fetoprotein | 20,000 units IL-2 | 16.7 µg GM-CSF |
| pancreatic | 50 µg CEA | 50 µg CA 19-9 | 50 µg alpha Fetoprotein | 20,000 units IL-2 | 16.7 µg GM-CSF |
| ovarian | 1000 IU CA 125 | 50 µg alpha Fetoprotein | | 20,000 units IL-2 | 16.7 µg GM-CSF |
| colorectal | 50 µg CEA | 50 µg CA 19-9 | | 20,000 units IL-2 | 16.7 µg GM-CSF |

We claim:

1. A method for treating an individual comprising administering to an individual having a type of cancer, a therapeutically effective amount of a composition comprising about 50 µg PSA, about 2 µg CEA, about 1000 IU CA 125, about 20,000 units IL-2, and about 16.7 µg GM-CSF, per dose.

2. A method for inducing an immunotherapeutic response in an individual comprising administering to an individual diagnosed with a type of cancer a therapeutically effective amount of a composition comprising about 50 µg PSA, about 2 µg CEA, about 1000 IU CA 125, about 20,000 units IL-2, and about 16.7 µg GM-CSF, per dose, and wherein the type of the cancer is prostate cancer.

* * * * *